US012575837B2

(12) United States Patent
Reynolds

(10) Patent No.: US 12,575,837 B2
(45) Date of Patent: Mar. 17, 2026

(54) SYSTEMS AND METHODS FOR LASER ALIGNMENT CHECK IN SURGICAL GUIDANCE SYSTEMS

(71) Applicant: WRIGHT MEDICAL TECHNOLOGY, INC., Memphis, TN (US)

(72) Inventor: David G. Reynolds, Fairport, NY (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 510 days.

(21) Appl. No.: 17/822,536

(22) Filed: Aug. 26, 2022

(65) Prior Publication Data

US 2023/0116301 A1 Apr. 13, 2023

Related U.S. Application Data

(60) Provisional application No. 63/262,217, filed on Oct. 7, 2021.

(51) Int. Cl.
| | |
|---|---|
| *A61B 90/13* | (2016.01) |
| *A61B 17/15* | (2006.01) |
| *A61B 17/56* | (2006.01) |
| *A61B 34/20* | (2016.01) |

(52) U.S. Cl.
CPC .............. *A61B 17/15* (2013.01); *A61B 34/20* (2016.02); *A61B 90/13* (2016.02); *A61B 2017/568* (2013.01)

(58) Field of Classification Search
CPC .......................... A61B 90/13; A61B 2017/568
See application file for complete search history.

(56) References Cited

U.S. PATENT DOCUMENTS

| | | | |
|---|---|---|---|
| 8,882,777 B2 | 11/2014 | Heavener et al. | |
| 9,642,631 B2 | 5/2017 | Stemniski | |
| 9,649,117 B2 * | 5/2017 | Stemniski .......... | A61B 17/1739 |
| 2006/0036264 A1 * | 2/2006 | Selover ................. | A61B 90/11 |
| | | | 606/130 |
| 2007/0073296 A1 | 3/2007 | Panchbhavi | |
| 2010/0087829 A1 * | 4/2010 | Metzger ................. | A61B 34/10 |
| | | | 606/96 |

(Continued)

OTHER PUBLICATIONS

Leemrijse, et al., "The Quantum Total Ankle Prosthesis", Orthopaedic Surgery, Foot-Ankle Surgery, Foot and Ankle Institute, Brussels, BE, 2021, 36 pages.

(Continued)

*Primary Examiner* — David W Bates

(74) *Attorney, Agent, or Firm* — DUANE MORRIS LLP

(57) ABSTRACT

Various embodiments of an emitter-aligned surgical guide and methods of use are disclosed. The emitter-aligned surgical guide includes a body extending between a first surface and a second surface. The body defines at least one hole extending from the first surface to the second surface. At least one alignment jig is coupled to the second surface. The at least one alignment jig includes a jig arm extending from a first end coupled to the second surface of the body to a second end and an emitter support configured to couple an emitter device to the at least one alignment jig in a predetermined position relative to the body.

15 Claims, 12 Drawing Sheets

(56)        References Cited

U.S. PATENT DOCUMENTS

| | | | | |
|---|---|---|---|---|
| 2011/0106091 A1* | 5/2011 | Fisher | .................. | A61B 17/157 |
| | | | | 606/88 |
| 2011/0106092 A1* | 5/2011 | Fisher | .................. | A61B 17/157 |
| | | | | 606/88 |
| 2011/0208093 A1* | 8/2011 | Gross | ..................... | A61B 90/10 |
| | | | | 600/587 |
| 2012/0245589 A1* | 9/2012 | Fisher | .................... | A61B 90/11 |
| | | | | 606/87 |
| 2012/0296401 A1* | 11/2012 | Potts | ..................... | A61B 90/11 |
| | | | | 607/90 |
| 2014/0257307 A1* | 9/2014 | Johannaber | ........ | A61B 17/1714 |
| | | | | 606/88 |
| 2014/0257308 A1* | 9/2014 | Johannaber | ............ | A61B 17/66 |
| | | | | 606/88 |
| 2015/0080740 A1* | 3/2015 | Hao | ....................... | A61B 90/11 |
| | | | | 600/476 |
| 2017/0112586 A1* | 4/2017 | Dhupar | ............... | A61B 17/808 |

OTHER PUBLICATIONS

Paragon 28, Laser-Focused Seniors Design Ankle Alignment Accuracy, Feb. 21, 2020, 4 pages.
Paragon 28, "Maven Patient Specific Surgery, Patient-Specific Instrumentation Surgical Technique Guide, Apex 3D", 2021, 36 pages.

* cited by examiner

SYSTEMS AND METHODS FOR LASER ALIGNMENT CHECK IN SURGICAL GUIDANCE SYSTEMS

CROSS-REFERENCE TO RELATED APPLICATION

This application claims priority under 35 U.S.C. § 119(e) to U.S. Provisional Application No. 63/262,217, filed on Oct. 7, 2021, the entire contents of which are incorporated herein by reference.

TECHNICAL FIELD

This application relates generally to surgical guide systems and, more specifically, to laser alignment of surgical guidance systems.

BACKGROUND

Many surgical procedures, including revision procedures, employ the use of aligned surgical guides. When using patient specific alignment guides that surface match on a bone or other anatomy, the feeling of a locked on fit is the primary feedback to the surgeon that the guide has been placed in the correct position. The fit of the guide on the bone is somewhat nuanced with a subtle feel. This fit and feel feedback has potential accuracy errors. Accuracy is typically found to be within 2° and within ~2 mm of the intended alignment and placement. Secondary checks are currently used to confirm guide placement accuracy.

Current state of the art secondary checks fall under two categories: physical external references such as a drop rod that goes through a hole feature in the guide that can be used for physical visual comparison to the anatomy, or a similar rod that can be used in conjunction with an x-ray or fluoroscopy. In both cases the rod or other device is compared against the anatomy visible in the field of view to confirm accuracy of the guide placement before proceeding to the next steps of the surgical procedure. Current check systems have a number of drawbacks, including subjecting users and patients to potentially hazardous ionizing radiation, having to place fixation pins through the guide into the bone to secure the guide placement prior to ensuring correct alignment, adding physical bulk and weight which may negatively affect the delicate tactile feel of the guide fit, and loss of patient-specific alignment options.

SUMMARY

In various embodiments, an emitter-aligned surgical guide is disclosed. The emitter-aligned surgical guide includes a body extending between a first surface and a second surface. The body defines at least one hole extending from the first surface to the second surface. At least one alignment jig coupled to the second surface. The at least one alignment jig includes a jig arm extending from a first end coupled to the second surface of the body to a second end and an emitter support configured to couple an emitter device to the at least one alignment jig in a predetermined position relative to the body.

In various embodiments, a system including an emitter-aligned surgical guide, at least one fixation element, and at least one additional surgical guide is disclosed. The emitter-aligned surgical guide includes a body extending between a first surface and a second surface. The body defines at least one hole extending from the first surface to the second surface. At least one alignment jig coupled to the second surface. The at least one alignment jig includes a jig arm extending from a first end coupled to the second surface of the body to a second end and an emitter support configured to couple an emitter device to the at least one alignment jig in a predetermined position relative to the body. The at least one fixation element is sized and configured to be received within the at least one hole defined by the body of the emitter-aligned surgical guide. The at least one additional surgical guide is configured to be coupled to one of the emitter-aligned surgical guide or the at least one fixation element.

In various embodiments, a method is disclosed. The method includes a step of positioning an emitter-aligned surgical device adjacent to a first anatomical location. The emitter aligned surgical device includes a body extending between a first surface and a second surface and a first alignment jig coupled to the second surface. The body of the emitter-aligned surgical device includes at least one hole extending from the first surface to the second surface. The first alignment jig includes a jig arm extending from a first end coupled to the second surface of the body to a second end and an emitter support coupled to a first emitter device. The first alignment jig positions the first emitter device in a predetermined position relative to the body. The method further includes steps of generating an emitted mark from the first emitter device and positioning the emitter-aligned surgical device at the first anatomical location such that the emitted mark from the first emitter device is aligned at a predetermined second anatomical location.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
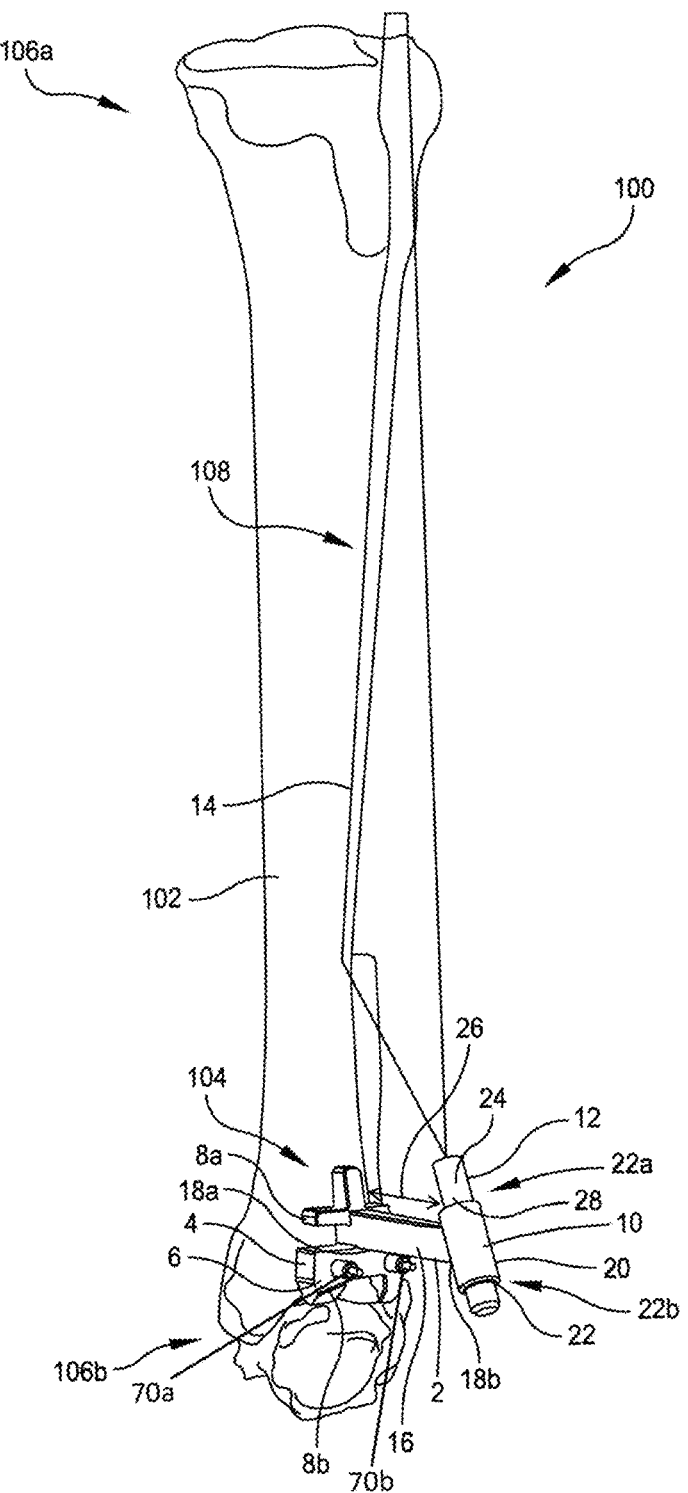
FIG. 1 illustrates a target site including a surgical guide having a laser alignment jig attached thereto, in accordance with some embodiments.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a emitter-aligned surgical guide including a patient-specific surface configured to couple the laser alignment jig to a target site and at least one emitter support configured to couple an visible emitter, such as a laser, to the laser alignment jig. In some embodiments, the target site is patient-specific and a patient-specific surface defines a surface architecture that is an opposite of and configured to couple to at least one first anatomical structure of a patient at the target site. In other embodiments, the surgical guide is a universal guide configured to couple to one or more prepared surgical sites. When an emitter is coupled to the emitter support, the emitter generates an emitted marker that references at least one second predetermined anatomical structure of a patient when the emitter-aligned surgical guide is properly coupled to the patient anatomy. The emitted marker may include a point (e.g., dot), a line, an area, and/or any other suitable planar and/or linear shape. The emitted marker my indicate a path of an implant based on one or more cuts formed using the laser alignment jig and/or another jig positioned in conjunction with or subsequent to the laser alignment jig.

Figure 2:
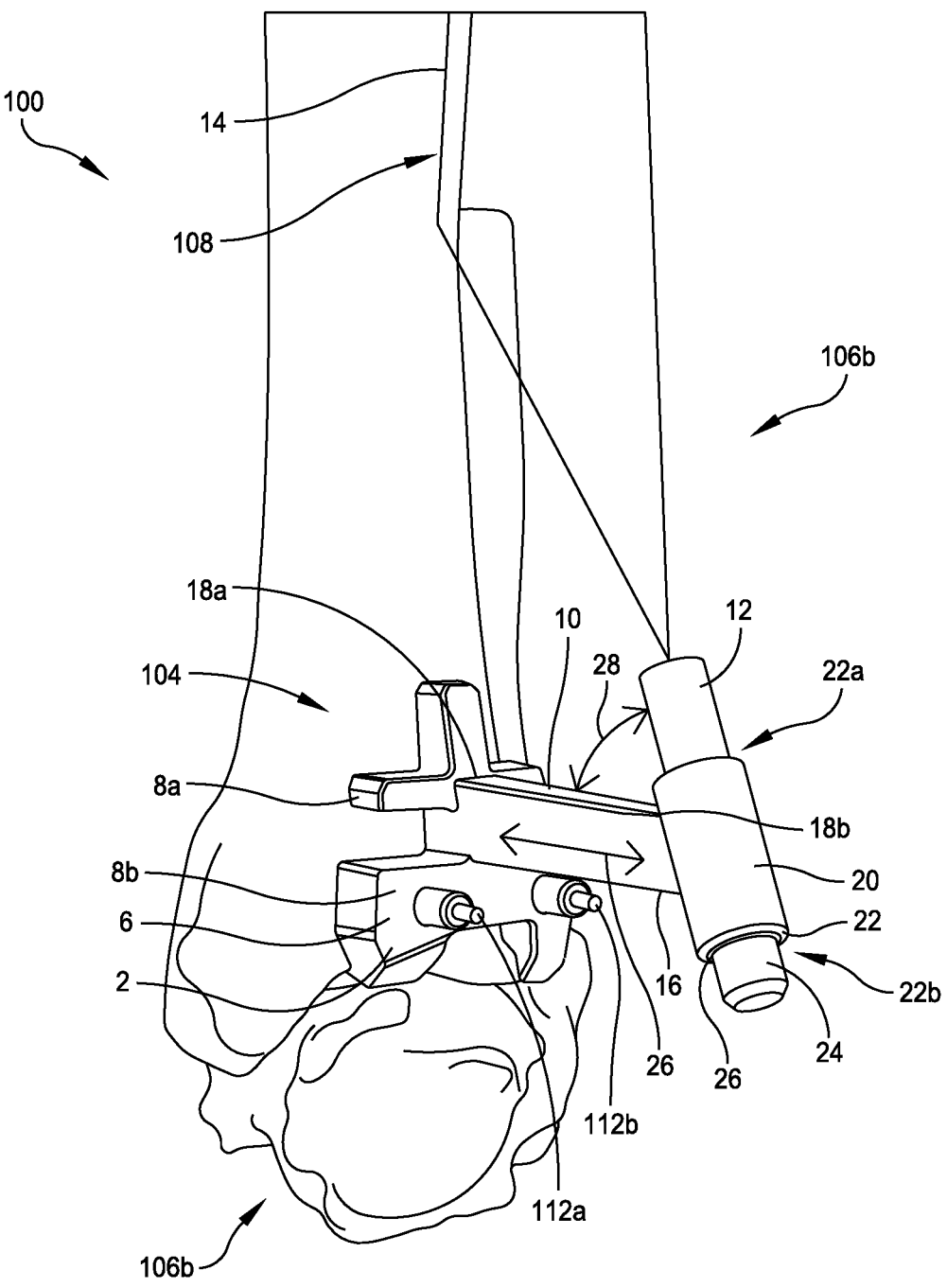
FIG. 2 illustrates the distal portion of the target site of FIG. 1, in accordance with some embodiments.

FIG. 1 illustrates a target site 100 having an emitter-aligned surgical guide 2 coupled thereto, in accordance with some embodiments. FIG. 2 illustrates a distal portion 106*b* of the target site 100 of FIG. 1, in accordance with some embodiments. The emitter-aligned surgical guide 2 includes a coupling portion 4 having a body 6. The body 6 has a thickness extending between a first surface 8*a* and a second surface 8*b*. In some embodiments, the first surface 8*a* includes a patient-specific topography that is configured to match and couple to a first anatomical location 104 having a patient-specific anatomical topography. In some embodiments, the first anatomical location 104 is a portion of an anatomical structure 102 such as a bone, for example, a distal end of a tibia. Although embodiments are discussed herein including patient-specific topographies, it will be understood that the emitter-aligned surgical guide 2 may include universal surfaces configured to interface with and/or couple to anatomical structure of a patient that have been prepared for the interface (for example, through sawing, cutting, reaming, etc.) and/or that interface with anatomical structures without consideration of patient-specific alignments.

The patient-specific topography is configured to position the emitter-aligned surgical guide 2 at a predetermined position with respect to the first anatomical location 104. The first surface 8*a* provides feedback to a surgeon (or other user) when the guide has been placed correctly with respect to the first anatomical location 104. In some embodiments, the first surface 8*a* provides a fit within about 2° and within about 2 mm of a an intended (or ideal) alignment and placement.

In some embodiments, the emitter-aligned surgical guide 2 includes an emitter alignment jig 10 configured to support an emitter element 12. The emitter element 12 is configured to generate an emitted marker 14 to facilitate additional alignment of the emitter-aligned surgical guide 2. The emitter alignment jig 10 includes a jig arm 16 extending from a first end 18*a*, coupled to the second surface 8*a* of the body 6, to a second end 18*b*. An emitter support 20 is coupled to the second end 18*b* of the jig arm 16. The emitter support 20 is configured to support an emitter element 12 in a predetermined position and at a predetermined orientation with respect to the coupling portion 4 of the emitter-aligned surgical guide 2. The jig arm 16 is configured to position the emitter element 12 at a predetermined distance 16 with respect to the second surface 8*b* of the body 6.

In some embodiments, the emitter support 20 defines a hollow cylinder 22 extending from a first end 22*a* to a second end 22*b*. The hollow cylinder 22 defines an internal opening or channel sized and configured to receive the emitter element 12 at least partially therethrough. In some embodiments, the internal channel defined by the hollow cylinder 22 is tapered or stepped to allow a portion of the emitter element 12 to be inserted into the holder to a predetermined position and to hold the emitter element 12 in the predetermined position. In some embodiments, the internal channel defines a constant diameter and the emitter element 12 includes a tapered or stepped outer surface 24 configured to allow insertion of the emitter element 12 up to a predetermined depth within the internal channel of the hollow cylinder 22.

In some embodiments, the jig arm 16 positions the emitter support 20 a predetermined distance from the coupling portion 4 of the emitter-aligned surgical guide 2 and the emitter support 20 is coupled to the jig arm 16 at a predetermined angle 28. The combination of the predetermined distance 26 and the predetermined angle 28 causes an emitter element 12 coupled to the emitter support 20 to project an emitted marker 14 in a predetermined pattern with respect to the emitter-aligned surgical guide 2. When the emitter-aligned surgical guide 2 is coupled to the anatomical structure 102 in a predetermined (e.g., ideal) position, the emitter element 12 is positioned to project the emitted marker 14 at a predetermined position with respect to a second anatomical structure or location 108.

The referenced second anatomical location 108 is defined by the distance 26 between the emitter support 20 and the coupling portion 4, the angle 28 between the emitter support 20 and the jig arm 16, and the pattern of the emitted marker 14 generated by the emitter element 12. For example, in the embodiment illustrated in FIGS. 1-2, the emitted marker 14 defines a line which is positioned such that the emitted marker 14 extends from a mid-portion of a shaft to the proximal end 106*a* of the anatomical structure 102, i.e., a tibia. The emitted marker 14 is positioned to reference a central axis of the shaft and a tuberosity. As discussed in further detail below the emitted marker 14 may include a dot configured to reference a specific anatomical location and/or an area configured to reference an anatomical structure in whole or in part. The emitted marker 14 may be selected to provide an indication in one or more degrees of freedom, such as, for example, a varus/valgus alignment, flexion, etc.

In some embodiments, the emitter support 20 and/or the jig arm 16 are configured to provide movement of the emitter element 12 in one or more predetermined degrees of freedom (e.g., directions of movement, rotational directions, etc.) to move the emitted marker 14 in a predetermined pattern. For example, in some embodiments, the emitter support 20 may be coupled to the jig arm 16 by a pivot allowing the emitter support 20 (and an emitter element 12 coupled thereto) to sweep (or move) in a first plane. Although specific embodiments are discussed herein, it will be appreciated that any suitable movement of the emitter marker 14 may be facilitated by movement of the emitter support 20 and/or the jig arm 16 in any one or more degrees of movement/freedom.

In some embodiments, the emitted marker 14 is configured to provide alignment (e.g., primary or secondary) of the emitter-aligned surgical guide 2 with respect to the first anatomical location 104. The emitter-aligned surgical guide 2 may be initially coupled to the first anatomical location 104 based on a fit between the first surface 8*a* and the anatomical topography of the first anatomical location 104. Simultaneous with and/or after positioning the emitter-aligned surgical guide 2 using the first surface 8*a*, the emitter-aligned surgical guide 2 is further adjusted to position the emitted marker 14 in a predetermined position that references the second anatomical location 108. When the emitted marker 14 is positioned at the predetermined second anatomical location 108, the emitter-aligned surgical guide 2 is in a predetermined position with respect to the first anatomical location 104 and one or more surgical procedures maybe performed using the emitter-aligned surgical guide 2. For example, in some embodiments, the emitter-aligned surgical guide 2 is a cutting guide configured to assist or guide the formation of at least one cut in the anatomical structure 102. In some embodiments, the emitter-aligned surgical guide 2 is coupled to the anatomical structure 102, for example, by one or more coupling elements 112*a*, 112*b* inserted through the body 6 and into the anatomical structure 102.

In some embodiments, the second anatomical location 108 is located at a predetermined distance from the first anatomical location 104 such that small deviations, such as small angular or positional deviations, result in greater movement of the emitted marker 14. In the illustrated embodiment, the second anatomical location 108 is a proximal end of a tibia, which is spaced apart from the first anatomical location 104, e.g., a distal end of a tibia, by the length of the shaft of the tibia. As will be appreciated, and discussed in greater detail below, the second anatomical location 108 may be positioned at a greater distance, such as, for example, proximal to a knee, at a hip, and/or any other location at a sufficient distance from the distal end of the tibia. In some embodiments, the second anatomical location includes a fluoroscopic marker or other target body coupled to, formed on, and/or otherwise interfaced with a patient anatomy and/or a surgical theatre that provides reference points with respect to one or more anatomical structures of a patient.

In some embodiments, the second anatomical location 108 may be replaced with a fixed, non-anatomical location separate from the target site 100. For example, in some embodiments, the second location may include a fixed point in a surgical room, on an operating table, and/or otherwise providing a fixed reference point with respect to the first anatomical location 104 and the emitter-aligned surgical guide 2.

In some embodiments, a portion of the emitted marker 14 may be configured to guide one or more surgical operations, such as, for example, a cutting or drilling operation. The emitted marker 14 may be projected onto the target site 100 to represent the location of an implant (or portion of an implant), a cut or opening required for insertion of an implant, and/or any other reference point configured to provide guidance to a surgeon in preparing a target site 100 for an implant. In some embodiments, the emitted marker 14 may indicate a placement location for a second surgical guide, such as a saw guide, configured to facilitate one or more surgical operations. In some embodiments, the emitter marker 14 itself serves as a guide, such as, for example, projecting a line to be cut.

In some embodiments, the emitter alignment jig 10 may be omitted and the emitter element 12 and/or the emitter support 20 may be formed integrally with the body 6 of the coupling portion 4. For example, in some embodiments, the body 6 may define an opening sized and configured to receive an emitter element 12 therein. As another example, in some embodiments, an emitter element 12 may be formed integrally with the body 6 during a body-formation process (such as a molding process). The body 6 may define an opening sized and configured to allow an emitted marker 14 to exit the body and intersect the second anatomical location 108.

In some embodiments, the body 4 of the emitter-aligned surgical guide 2 includes one or more holes 70*a*, 70*b* extending therethrough. The holes 70*a*, 70*b* are sized and configured to receive a fixation element, such as a k-wire, pin, etc., therethrough. The fixation elements couple the body 4 of the emitter-aligned surgical guide 2 to the first anatomical location 102. In some embodiments, the fixation elements may be inserted through the holes 70*a*, 70*b* and into one or more bones or other structures at the first anatomical location 102 prior to, during, and/or after alignment of the emitter-aligned surgical guide 2 is confirmed using the emitted marker 14. The emitted mark 14 allows proper alignment of the emitter-aligned surgical guide 2 prior to insertion of any surgical elements, such as k-wires, into the patient's anatomical structure, reducing the number of steps required during surgery and potentially eliminating additional holes in a patient's anatomy (either due to misplacement of surgical elements and/or eliminating the need for fixation elements). Alignment with various anatomical structures may be confirmed by alignment with surface marks formed on a patient, visible internal anatomy, 2D x-ray images, and/or any other suitable method.

Figure 3:
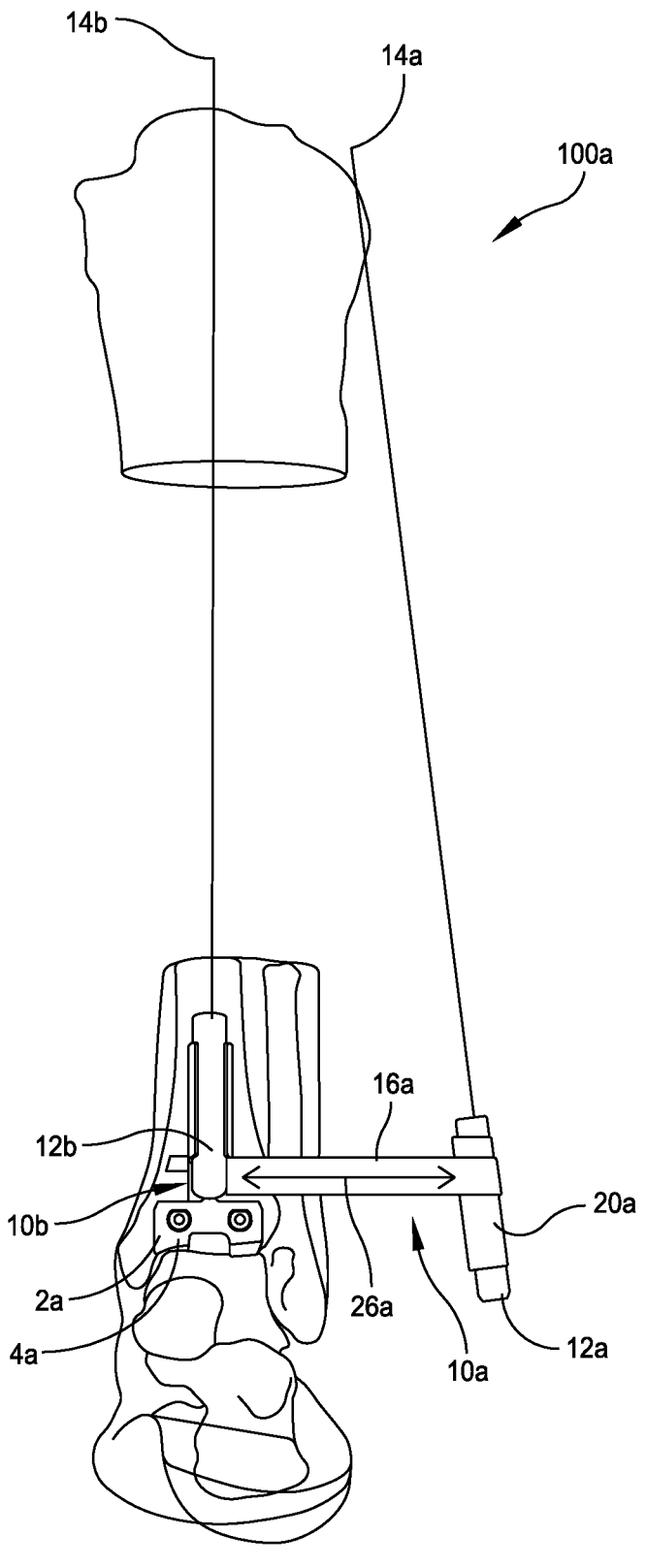
FIG. 3 illustrates a target site including a surgical guide having a dual-laser alignment jig attached thereto, in accordance with some embodiments.
Figure 4:
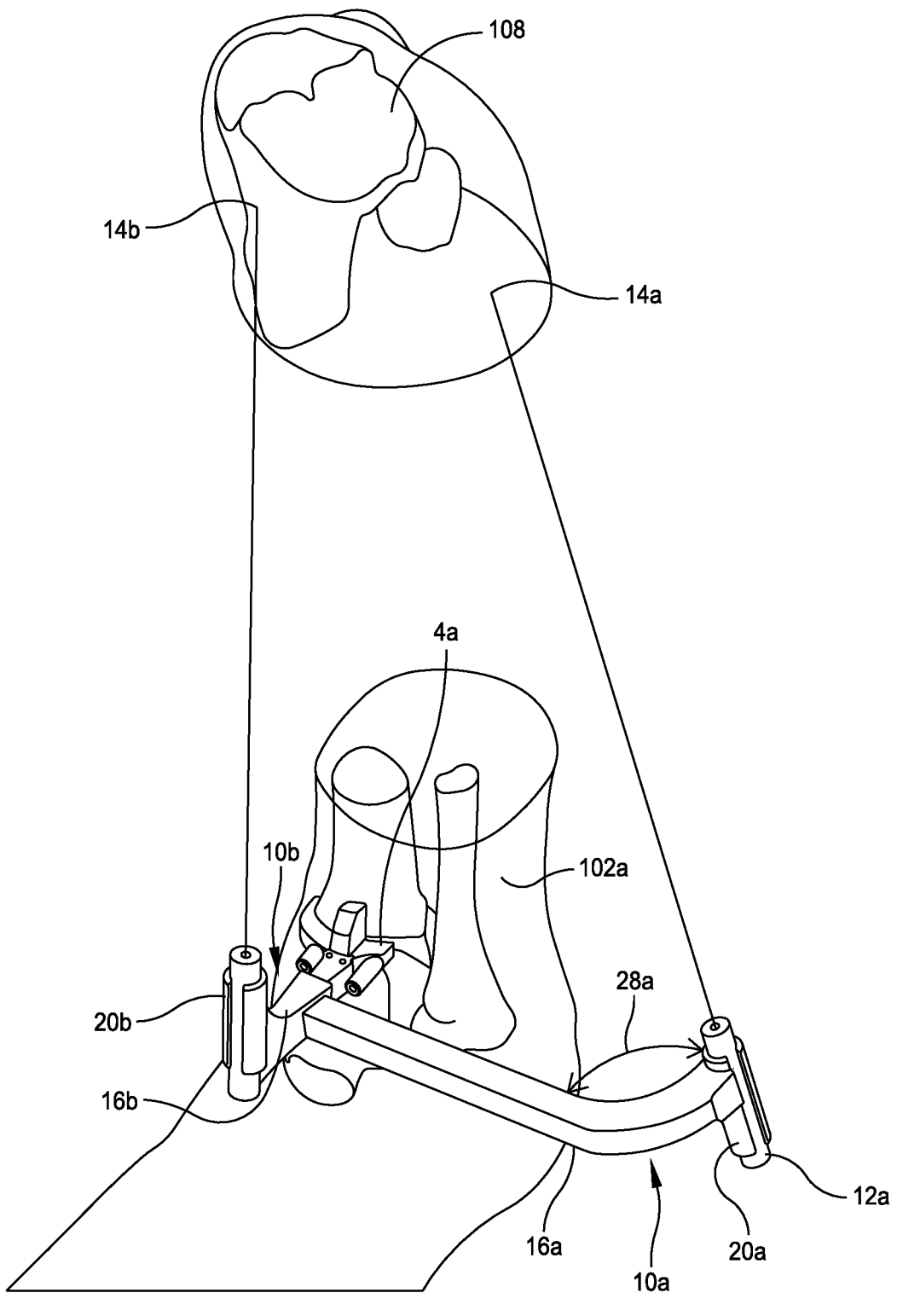
FIG. 4 illustrates a perspective view of the target site and surgical guide of FIG. 3, in accordance with some embodiments.
Figure 5:
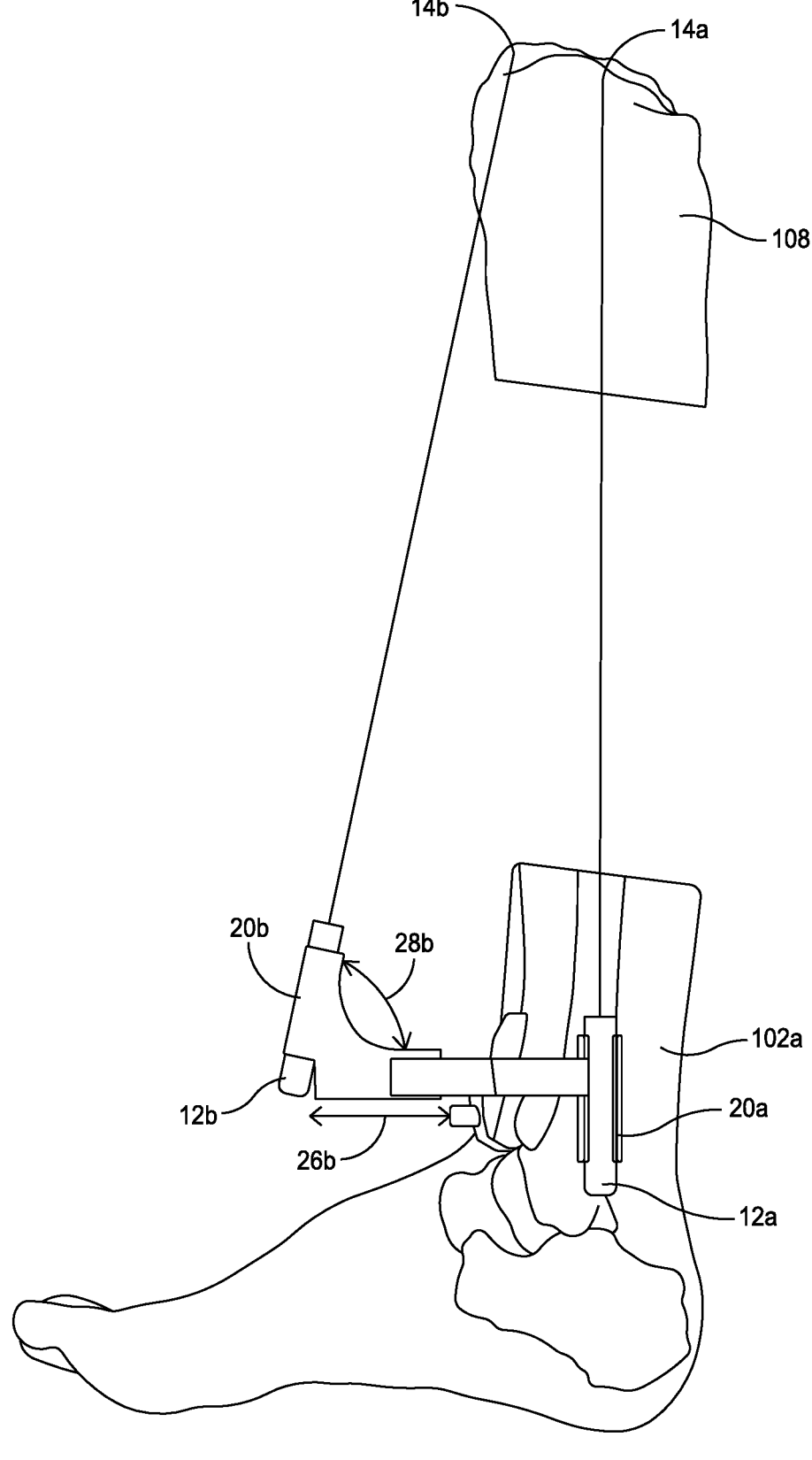
FIG. 5 illustrates a side view of the target site and surgical guide of FIG. 3, in accordance with some embodiments.

FIGS. 3-5 illustrate a target site 100*a* including an emitter-aligned surgical guide 2*a* having a first emitter alignment jig 10*a* and a second emitter alignment jig 10*b* coupled thereto, in accordance with some embodiments. The target site 100*a* and the emitter-aligned surgical guide 2*a* are similar to the target site 100 and emitter-aligned surgical guide 2 discussed above, and similar description is not repeated herein. The emitter-aligned surgical guide 2*a* includes a first emitter alignment jig 10*a* configured to position a first emitter element 12*a* in a first position and a second emitter alignment jig 10*b* configured to position a second emitter element 12*b* in a second position. The first and second emitters 12*a*, 12*b* are each configured to generate at least one respective emitted marker 14*a*, 14*b*.

In some embodiments, the jig arm 16*a* of the first emitter alignment jig 10*a* positions an emitter support 20*a* at a first predetermined distance 26*a* in a first direction from the coupling portion 4*a* of the emitter-aligned surgical guide 2*a*. The emitter support 20*a* may be coupled to the jig arm 16*a* at a first predetermined angle 28*a*. The jig arm 16*b* of the second emitter alignment jig 10*b* positions an emitter support 20*b* at a second predetermined distance 26*b* in a second direction from the coupling portion 4*a*. The emitter support 20*b* may be coupled to the jig arm 16*b* at a second predetermined angle 28*b*. A first emitter element 12*a* coupled to the first emitter support 20*a* projects a first emitted marker 14*a* in a first predetermined pattern with respect to the emitter-aligned surgical guide 2*a* and a second emitter element 12*b* coupled to the second emitter support 16*b* projects a second emitter marker 14*b* in a second predetermined pattern. When the emitter-aligned surgical guide 2*a* is coupled to the anatomical structure 102*a* in a predetermined (e.g., ideal) position, the first emitter element 12*a* is positioned to project the first emitted marker 14*a* to a first predetermined position with respect to a second anatomical structure or location 108 and the second emitter element 12*b* is positioned to project the second emitted marker 14*b* to a second predetermined position with respect to the second anatomical structure or location 108. The first emitted marker 14*a* and the second emitted marker 14*b* may be positioned in distinct planes to simultaneously coordinate between multiple anatomical targets and/or fluoroscopic markers.

In some embodiments, the first emitter element 12*a* is positioned to generate a first emitted marker 14*a* in a first plane and the second emitter element 12*b* is positioned to generate a second emitted marker 14*b* in a second plane. For example, in some embodiments, the first emitted marker 14*a* is configured to provide alignment information in a first plane such as a mid-coronal plane and a second emitted marker 14*b* is configured to provide alignment information in a second plane such as a mid-sagittal plane. Although specific embodiments are discussed herein, it will be appreciated each of the emitted markers 14*a*, 14*b* may be configured to provide alignment in one or more planes and/or one or more degrees of movement.

Figure 6:
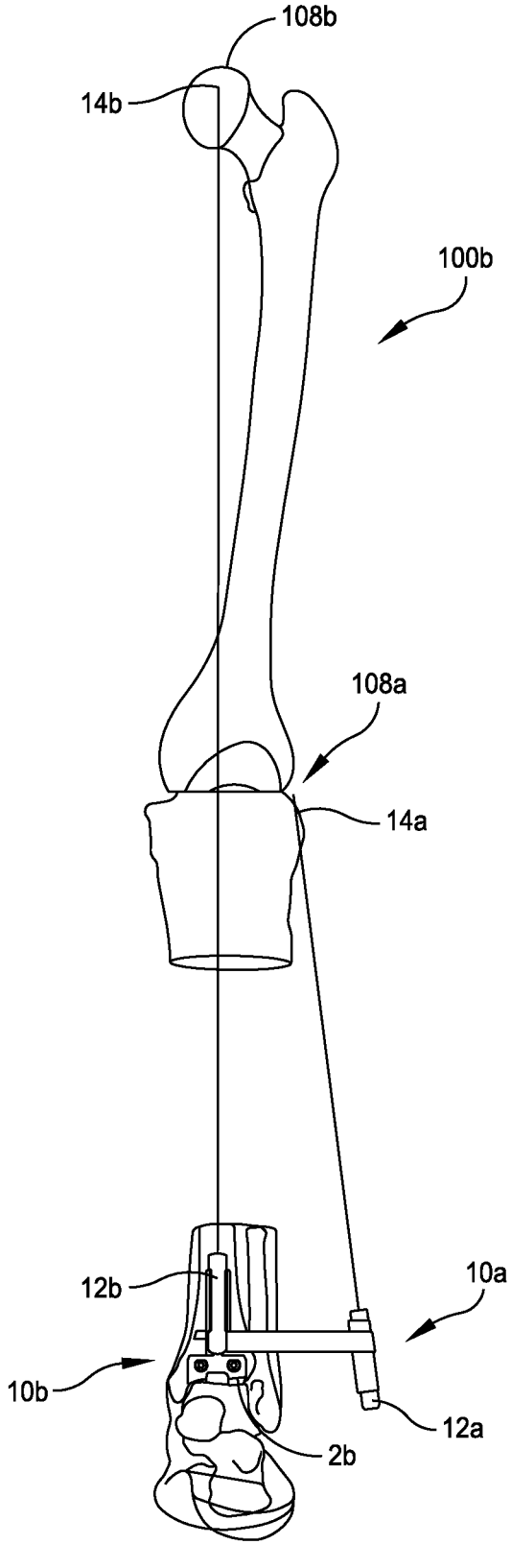
FIG. 6 illustrates a target site including a surgical guide having a dual-laser alignment jig including at least one laser configured to reference a second anatomical structure, in accordance with some embodiments.

In some embodiments, the first emitted marker 14*a* and/or the second emitted marker 14*b* may each be configured to reference a specific, predetermined anatomical location. For example, in some embodiments, the first emitted marker 14*a* may be configured to project a predetermined pattern (such as a dot) onto a second predetermined anatomical location and the second emitted marker 14*b* may be configured to project a predetermined pattern (such as a dot) onto a third predetermined anatomical location. For example, as illustrated in FIG. 6, the second anatomical location 108*a* is a tibia tubercle and the third anatomical location 108*b* is a proximal fibular head, although it will be appreciated that any suitable anatomical locations 108*a*, 108*b* may be used based on the first anatomical location 104.

In some embodiments, the first emitted marker 14*a* and/or the second emitted marker 14*b* may be configured to pass near to an anatomical location and/or structure without interacting with the anatomical structure or location, for example, as discussed in greater detail below with respect to FIG. 7. One or more of the emitted markers 14*a*, 14*b* may include a pattern that is configured to be close to, but not interact with, the anatomical structure or location when the emitter-aligned surgical guide 2*a* is properly aligned. In such embodiments, if the emitter marker 14*a*, 14*b* intersects an anatomical structure, the emitter-aligned surgical guide 2*a* is not in a predetermined position with respect to the first anatomical location 104 and can be adjusted accordingly.

In some embodiments, a single emitter element 12*a* may be used to generate both the first emitted marker 14*a* and the second emitted marker 14*b*. For example, in some embodiments, an emitter element 12*a* is coupled to the first emitter support 20*a* to project a first emitted marker 14*a*. The emitter-aligned surgical guide 2*a* may be aligned in at least one direction or plane indicated by the first emitted marker 14*a*. After the emitter-aligned surgical guide 2*a* is aligned in at least a first direction or plane, the emitter element 12*a* may be removed from the first emitter support 20*a* and coupled to the second emitter support 20*b* to project a second emitted marker 14*b*. The emitter-aligned surgical guide 2*a* may then be aligned in at least one direction or plane indicated by the second emitted marker 14*b*.

In some embodiments, a first emitted marker 14*a* and a second emitted marker 14*b* may be configured to represent size information corresponding to one or more implants configured to be used in conjunction with the emitter-aligned surgical guide 2*a*. The first emitter element 12*a* and the second emitter element 12*b* are spaced apart by the first emitter alignment jig 10*a* and the second emitter alignment jig 10*b*, respectively, at a known distance. The known distance may correspond to, for example, a size (e.g., width) an implant to be used in conjunction with the emitter-aligned surgical guide 2*a*, one or more resections or openings formed using the emitter-aligned surgical guide, and/or any other suitable distance. The first and second emitted markers 14*a*, 14*b* generated by the first and second emitter elements 12*a*, 12*b* may correspond to a size, path, location, etc. of an implant to be used, allowing comparison of implant size to the anatomy of the target site 100 prior to insertion of the implant.

FIG. 6 illustrates a target site 100*b* including an emitter-aligned surgical guide 2*b* having a first emitter alignment jig 10*a* and a second emitter alignment jig 10*b* coupled thereto, in accordance with some embodiments. The target site 100*b* and the emitter-aligned surgical guide 2*b* are similar to the target sites 100, 100*a* and emitter-aligned surgical guides 2, 2*a* discussed above, and similar description is not repeated herein. The emitter-aligned surgical guide 2*b* includes a first emitter alignment jig 10*a* configured to position a first emitter element 12*a* in a first position and a second emitter alignment jig 10*b* configured to position a second emitter element 12*b* in a second position. The first emitter element 12*a* is configured to project a first emitted marker 14*a* onto an anatomical location 108*a* positioned at a first proximal distance from the first anatomical location 104 and the second emitter element 12*b* is configured to project a second emitted marker 14*b* onto an anatomical location 108*b* positioned at a second proximal distance from the first anatomical location 104. The use of emitted markers 14*a*, 14*b* allows any specific anatomical structure to be referenced regardless of patient physical differences (e.g., height, weight, etc.).

In some embodiments, the anatomical location 108*a* identified by the first emitted marker 14*a* is positioned at a greater distance than the anatomical location 108*b* indicated by the second emitted marker 14*b*, although it will be appreciated that the distances may be reversed. For example, in the illustrated embodiment, the first emitted marker 14*a* is configured to intersect with an anatomical location 108*a* positioned at a hip and the second emitted marker 14*b* is configured to intersect with an anatomical location 108*b* positioned at a proximal end of the tibia. Although specific embodiments are illustrated herein, it will be appreciated that the anatomical location 108*a* referenced by the first emitted marker 14*a* and the anatomical location 108*b* referenced by the second emitted marker 14*b* may include any suitable anatomical locations having any predetermined spacing from the first anatomical location 104 and/or from each other.

Figure 7:
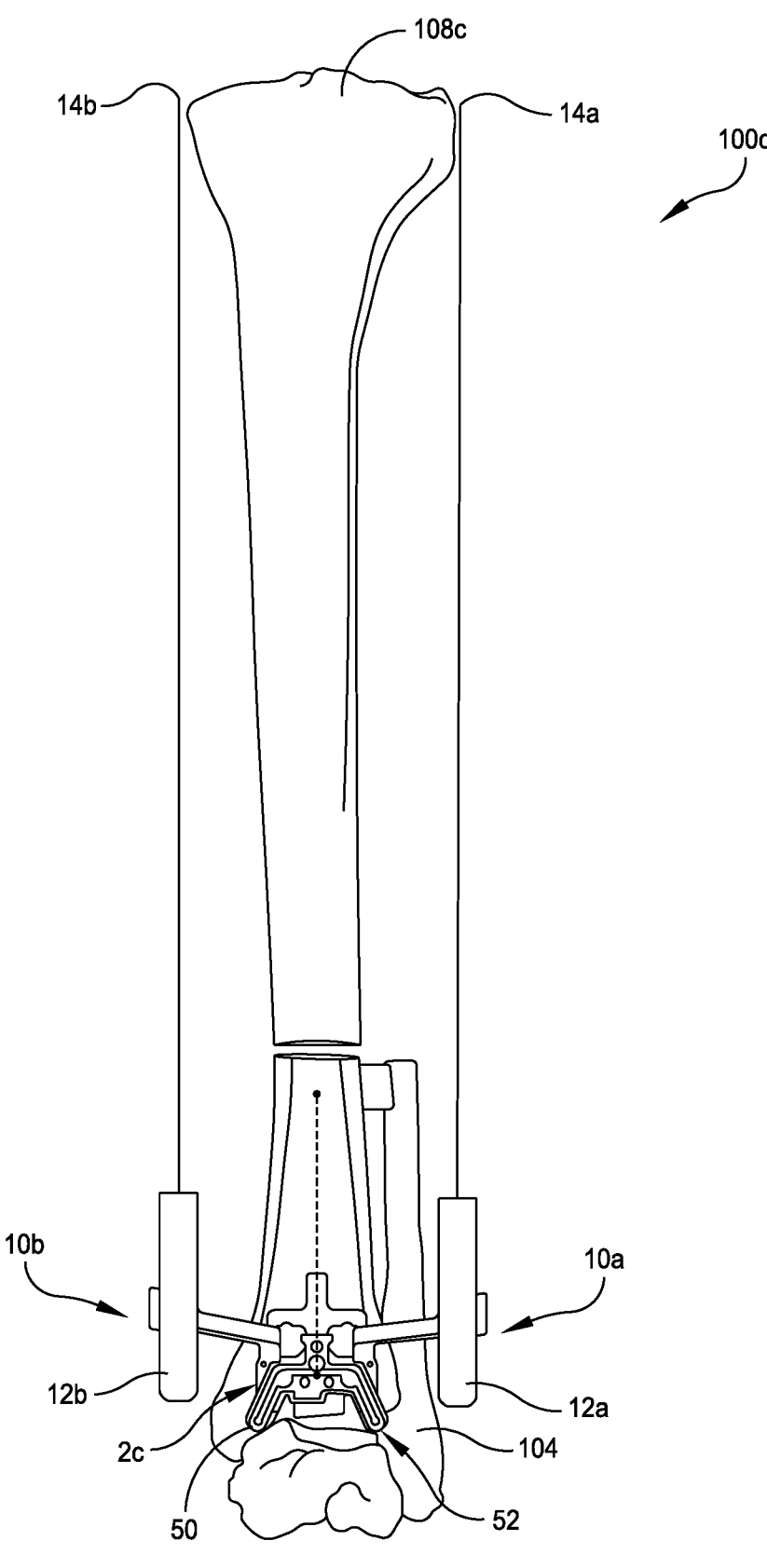
FIG. 7 illustrates a target site including a surgical guide having a goal-post alignment jig, in accordance with some embodiments.
Figure 8:
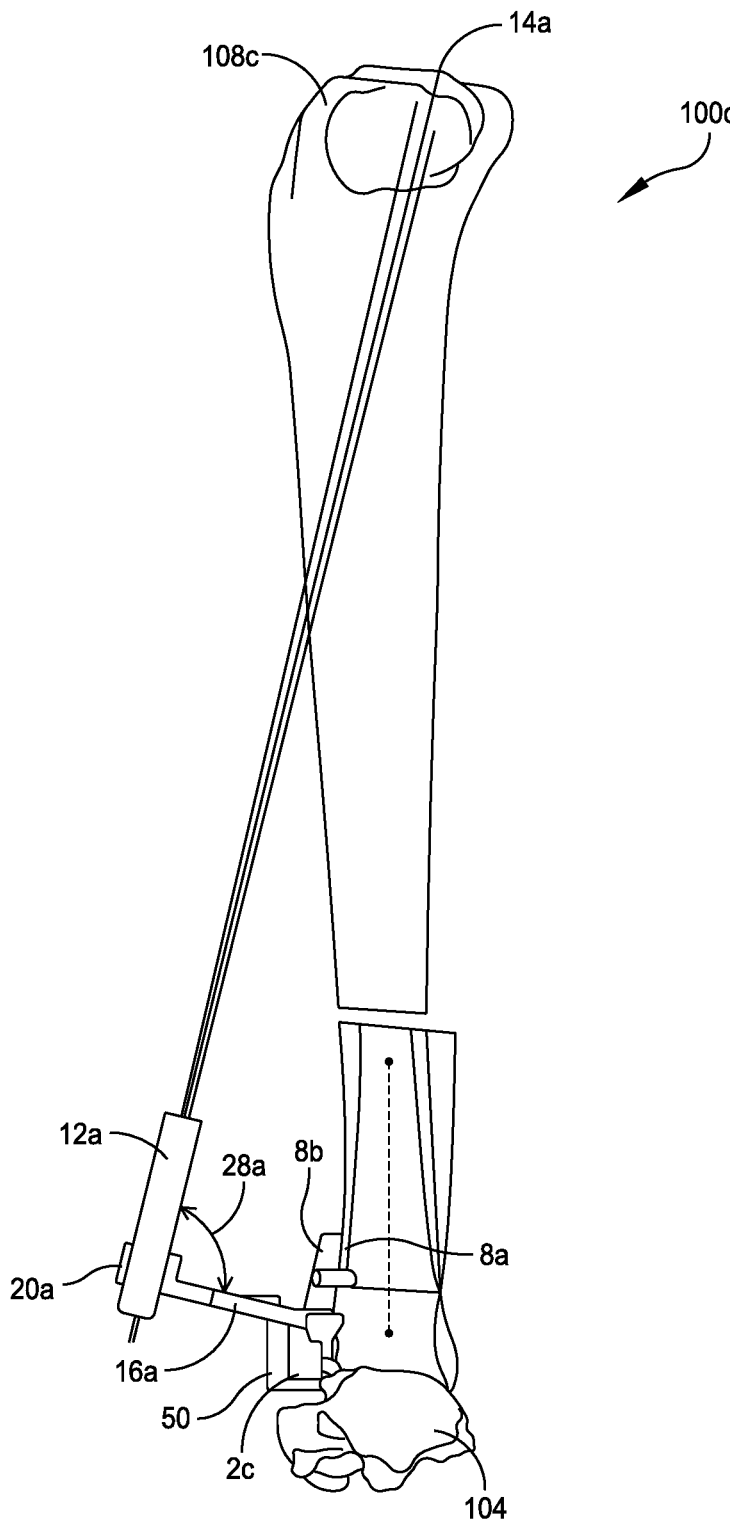
FIG. 8 illustrates a side view of the target site of FIG. 7 including the emitter-aligned surgical guide, in accordance with some embodiments.

FIGS. 7-8 illustrate a target site 100*c* including an emitter-aligned surgical guide 2*c* configured to position a first emitter element 12*a* and a second emitter element 12*b* to provide a goal-post alignment, in accordance with some embodiments. The target site 100*c* and the emitter-aligned surgical guide 2*c* are similar to the target sites 100, 100*a*, 100*b* and emitter-aligned surgical guides 2, 2*a*, 2*b* discussed above, and similar description is not repeated herein. The emitter-aligned surgical guide 2*c* includes a first emitter alignment jig 10*a* configured to position a first emitter element 12*a* in a first position and a second emitter alignment jig 10*b* configured to position a second emitter element 12*b* in a second position. The first and second emitter elements 12*a*, 12*b* are positioned to project respective first and second emitted markers 14*a*, 14*b* on either side of a predetermined anatomical location 108*c* in a "goal-post configuration."

In the illustrated embodiment, the first and second emitted markers 14*a*, 14*b* are configured to be positioned on either side of a proximal tibia 108*c* when the emitter-aligned surgical guide 2*c* is properly aligned with the first anatomical location 104 at a distal end of the tibia. In some embodiments, the first and second emitter elements 12*a*, 12*b* are positioned such that the second anatomical location 108*c* fits completely between the first and second emitted markers 14*a*, 14*b* when the emitter-aligned surgical guide 2*c* is properly aligned. In such embodiments, if either emitted marker 14*a*, 14*b* is intersecting a portion of the second anatomical location 108*c*, the emitter-aligned surgical guide 2*c* is not properly aligned at the first anatomical location 104. In other embodiments, the first and second emitted markers 14*a*, 14*b* may be configured to intersect specific anatomical landmarks on either side of an anatomical location 108*c*.

In some embodiments, the emitter-aligned surgical guide 2*c* is configured to be used by imaging one or more anatomical structures, such as the second anatomical location, using one or more medical imaging processes. For example, in various embodiments, a CT scan, MRI scan, X-ray, or other suitable medical imaging procedure may be used to obtain an image of one or more anatomical structures at the second anatomical location 108*c*.

In some embodiments, the emitter-aligned surgical guide 2*c* includes a surgical guide 50. The surgical guide 50 may be formed integrally with the emitter-aligned surgical guide 2*c*, permanently coupled to the emitter-aligned surgical guide 2*c*, and/or releasably coupled to the emitter-aligned surgical guide 2*c*. The surgical guide 50 may define one or more surgical paths 52 sized and configured to receive a surgical instrument therein. For example, in the illustrated embodiment, the surgical path 52 includes a cutting path sized and configured to receive a cutting instrument therethrough to form one or more cuts in the first anatomical structure 104 (and/or some other anatomical structure) when the emitter-aligned surgical guide 2*c* is properly aligned with the first and second anatomical structures 104, 108. As another example, in some embodiments, the surgical path 52 may define a path for insertion of a drill or reamer configured to form one or more holes in the anatomical structure 104 (and/or some other anatomical structure).

Figure 9:
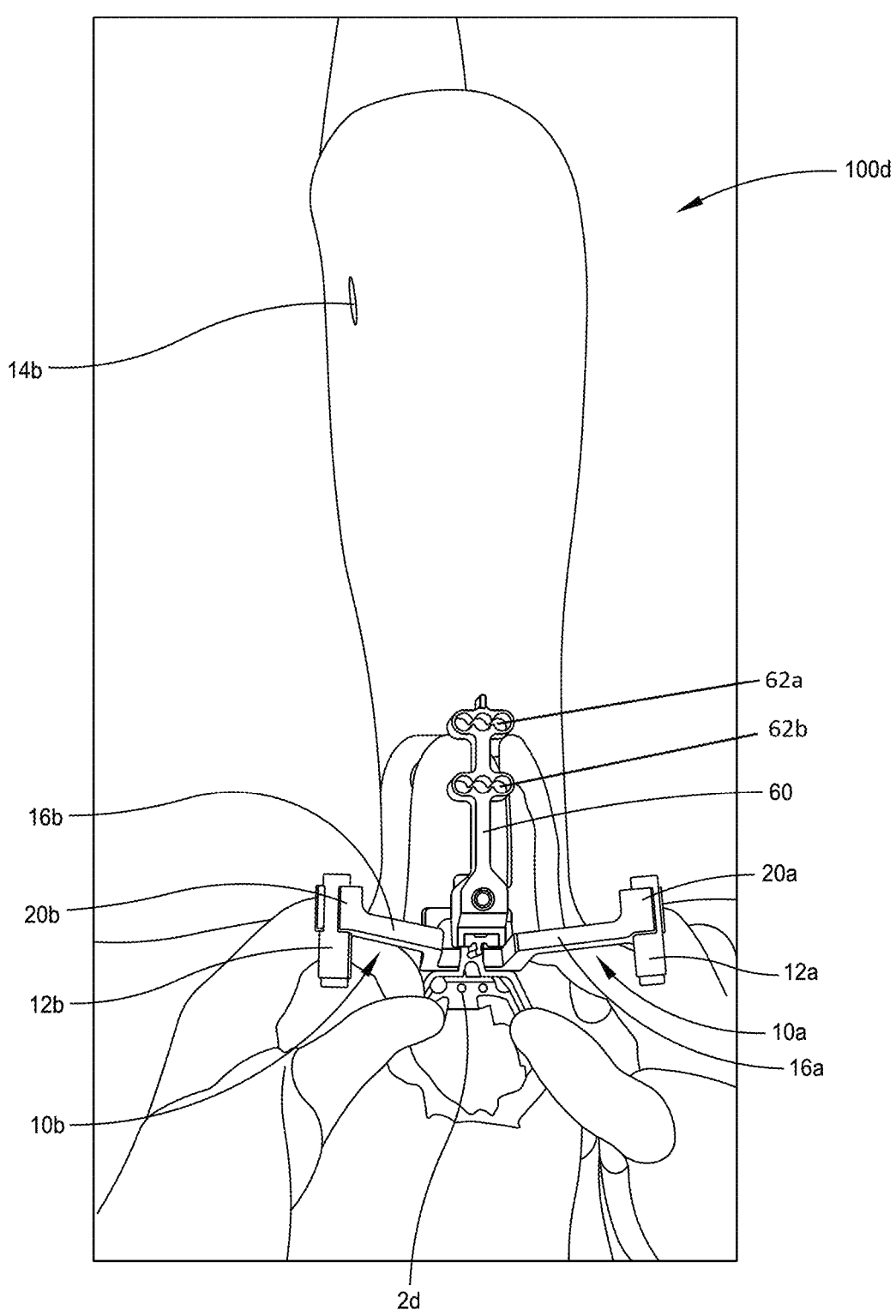
FIG. 9 illustrates a target site including an emitter-aligned surgical guide in an unaligned position with respect to a first anatomical location, in accordance with some embodiments.
Figure 10:
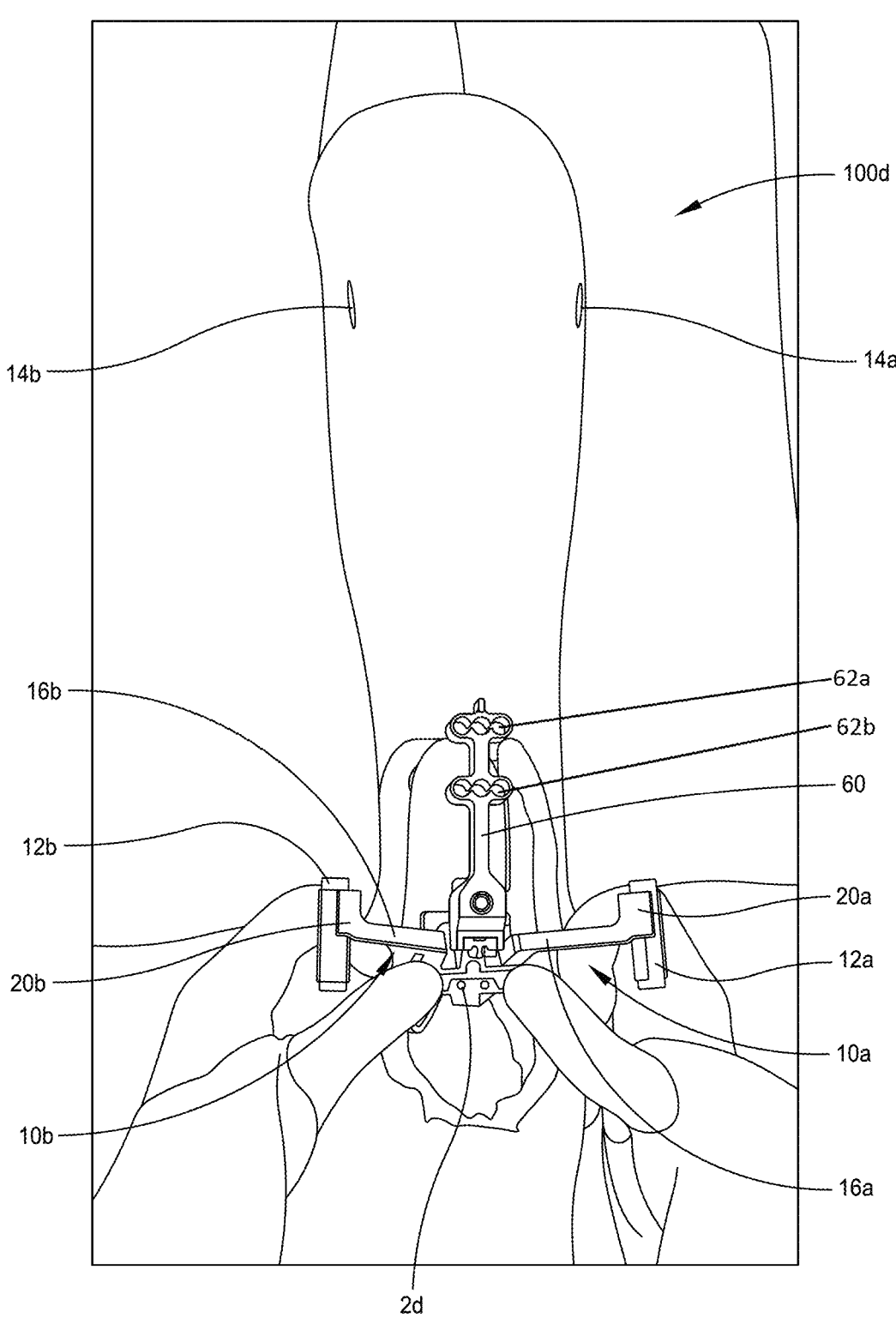
FIG. 10 illustrates the target site of FIG. 9 having the emitter-aligned surgical guide in an aligned position with respect to the first anatomical location, in accordance with some embodiments.

FIGS. 9-10 illustrate one embodiment of a emitter-aligned surgical guide 2*d* positioned at a surgical site 100*d*, in accordance with some embodiments. The target site 100*d* and the emitter-aligned surgical guide 2*d* are similar to the target sites 100, 100*a*, 100*b*, 100*c* and emitter-aligned surgical guides 2, 2*a*, 2*b*, 2*c* discussed above, and similar description is not repeated herein. The emitter-aligned surgical guide 2*d* includes a first alignment jig 10*a* having a first emitter 12*a* coupled thereto and a second alignment jig 10*b* having a second emitter 12*b* coupled thereto. The first and second emitters are configured in the "goal-post" configuration discussed above with respect to FIGS. 7-8.

FIG. 9 illustrates the emitter-aligned surgical guide 2*d* prior to alignment of a patient-specific surface, e.g., a first surface, with a patient's anatomy. As shown in FIG. 9, only a single emitter mark 14*b* (e.g., the medial marker) is visible at or near a second reference anatomical structure 108. The single emitter mark 14*b* is the only visible mark as the emitter-aligned surgical guide 2*d* is not properly aligned with the patient's anatomy. As shown in FIG. 10, when the emitter-aligned surgical guide 2*d* is properly aligned with the patient's anatomy and properly positioned to guide one or more surgical instruments to predetermined anatomical locations, a first emitter mark 14*a* (e.g., a lateral emitter mark) and a second emitter mark 14*b* (e.g., a medial emitter mark) are each visible at or near the second reference anatomical structure 108.

As illustrated in FIGS. 9-10, in some embodiments, a targeting guide 60 may be coupled to the emitter-aligned surgical guide 2*d*. The targeting guide 60 includes a plurality of targeting holes 62*a*-62*b* sized and configured to receive one or more elongate surgical instruments, such as a k-wire, therethrough. The targeting holes 62*a*, 62*b* guide the elongate surgical instruments to predetermined locations on the patient's anatomy to allow surgical elements, such as k-wires or guide wires, to be coupled to one or more anatomical structures to guide one or more further surgical procedures. For example, in the illustrated embodiment, the targeting guide 60 is configured to position one or more k-wires in a tibia for guiding additional surgical elements in a total ankle replacement surgery, although it will be appreciated that any suitable targeting guide 60 may be used with the emitter-aligned surgical guide 2*d*.

Figure 11:
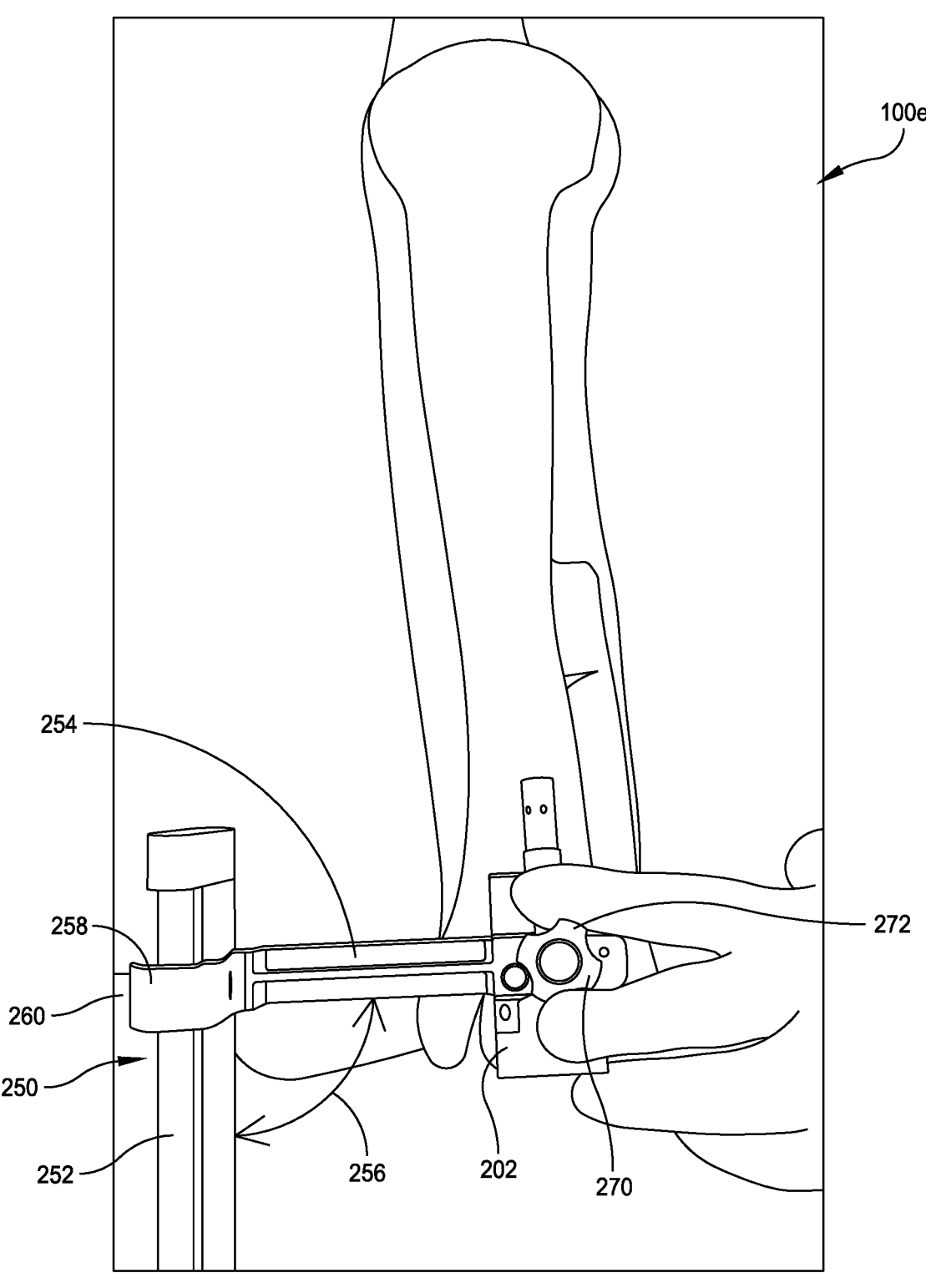
FIG. 11 illustrates a target site including an emitter-aligned surgical guide configured to be coupled to a support structure, in accordance with some embodiments.

FIG. 11 illustrates one embodiment of a surgical site 100*e* including an emitter-aligned surgical guide 202 including an offset guide mount 250, in accordance with some embodiments. The surgical guide 202 is similar to the surgical guides 2-2*d* discussed above, and similar description is not repeated herein. The emitter-aligned surgical guide 202 includes an offset guide mount 250 that positions a mount, such as mounting bar 252, outside of a working area of the surgical guide 202. In the illustrated embodiment, the offset guide mount 250 includes a mounting bar 252 coupled to an offset arm 254. The mounting bar 252 is configured to be coupled to one or more structures, such as an operating table, in a fixed and/or adjustable position. The offset arm 254 extends from the mounting bar 252 at a predetermined angle 256, such as, for example, an angle substantially between 30-90° (inclusive). Although specific embodiments are discussed herein, it will be appreciated that the predetermined angle 256 between the mounting bar 252 and the offset arm 254 may be a fixed and/or adjustable angle substantially between 0° and 180° (inclusive), such as, for example, about 15°-165°, 30°-150°, 45-135°, 60°-120°, such as, for example, 30°, 45°, 60°, 70°, 80°, 85°, 90°, 95°, 100°, 110°, 120°, 135°, 150°, etc.

In some embodiments, the offset arm 254 is slideably coupled to the mounting bar 252 such that a position of the offset arm 254 with respect to the surgical site 102e may be adjusted. For example, in the illustrated embodiment, the offset arm 254 is slideably coupled to the mounting bar 252 to allow adjustment of the offset arm 254 in the inferior/superior direction, although it will be appreciated that the mounting bar 252 may be configured to allow adjustments in other directions, such as the lateral/medial direction, the anterior/posterior direction, etc.

In some embodiments, the offset arm 254 includes a coupling mechanism 258 configured to couple the offset arm 254 to the mounting bar 252. In the illustrated embodiments, the offset arm 254 includes a coupling mechanism 258 at a lateral end 254a, although it will be appreciated that the coupling mechanism may be positioned at a medial end 254b of the offset arm 254 and/or positioned between the lateral end 254a and the medial end 254b. In some embodiments, the coupling mechanism 258 includes a locking mechanism 260 configured to fix or lock the position of the offset arm 254 with respect to the mounting bar 252. The locking mechanism 260 may include any suitable locking mechanism, such as, for example, a pin, a spring, a threaded locking mechanism, etc.

In some embodiments, the emitter-aligned surgical guide 2e is slideably coupled to the offset arm 254 such that the a position of the emitter-aligned surgical guide 2 may be adjusted with respect to the surgical site 102e and/or the mounting bar 252. In the illustrated embodiment, the emitter-aligned surgical guide 2e is adjustable in the medial/lateral direction, although it will be appreciated that the offset arm 254 may be configured to allow adjustment in other directions, such as the inferior/superior direction, the anterior/posterior direction, and/or any other suitable direction.

In some embodiments, the offset guide mount 250 includes a guide locking mechanism 270 configured to fixedly couple the emitter-aligned surgical guide 2e to the offset arm 254. The guide locking mechanism 270 may include any suitable locking mechanism, such as a threaded screw inserted through a hole defined in the offset guide mount 250 and into a threaded hole defined in the emitter-aligned surgical guide 2e. The locking mechanism 270 may include a knob 272 or other device for tightening the locking mechanism after positioning the emitter-aligned surgical guide 2e.

Figure 12:
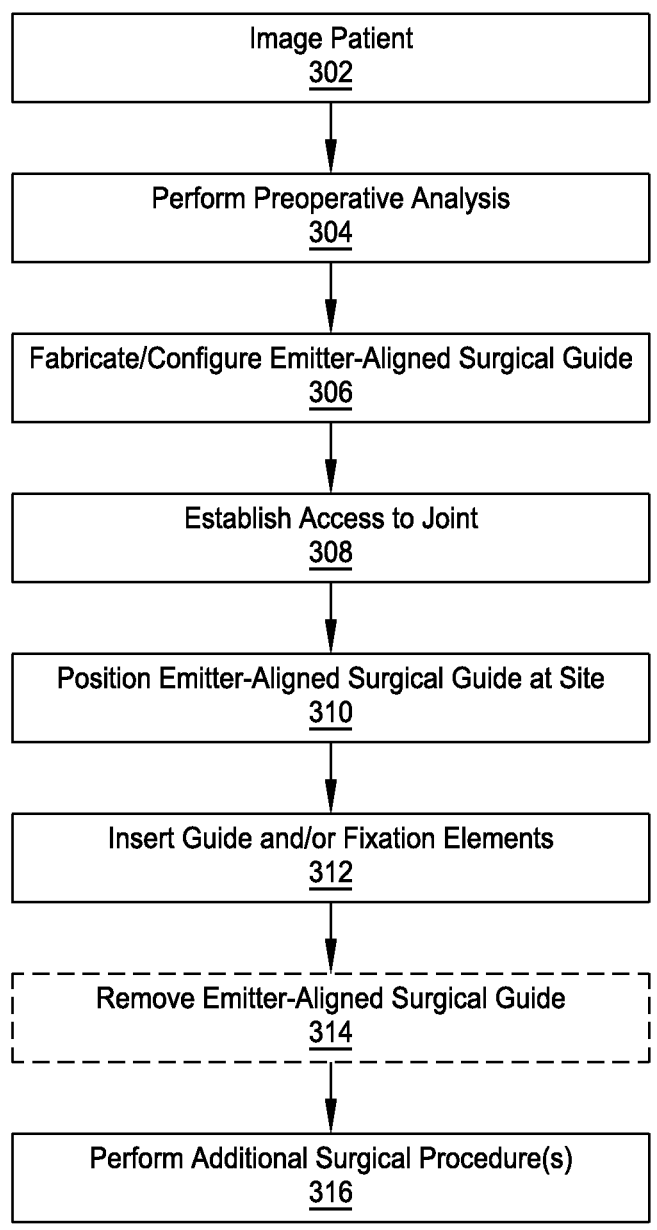
FIG. 12 is a flowchart illustrating a method of using an emitter-aligned surgical guide in various surgical procedures, in accordance with some embodiments.

The emitter-aligned surgical guides disclosed herein can be used in a wide variety of surgical methods, including joint replacement surgeries, revision surgeries, and fusion takedown surgeries, to name just a few. One example of a surgical procedure is described now with reference to FIGS. 1-8 and FIG. 12 in which FIG. 12 is a flowchart example of a method 300 in accordance with some embodiments. One of ordinary skill in the art will understand that various surgical procedures can be performed using the emitter-aligned surgical guides disclosed herein and therefore one or more steps of method 300 may be omitted and additional steps also can be performed.

At step 302, the patient is imaged. For example, one or more areas of a patient can be imaged using one or more medical imaging technologies such as x-ray, CT, and/or Mill to list only a few possibilities. In some embodiments, a single joint of the patient is imaged. For example, when the fusion takedown is to be performed on a patient's ankle, one or more images of the patient's ankle can be acquired using medical imaging instrumentation as will be understood by one of ordinary skill in the art.

However, in some embodiments, multiple joints of a patient are imaged in order to gather data concerning the patient's anatomy. For example, in order to be able to determine the anatomical and mechanical axes of the patient's leg, the patient's ankle and at least one other joint, e.g., knee or hip, also will be imaged.

At step 304, the image data is used to perform preoperative analysis of the surgical procedure. For example, the image data may be used to generate three-dimensional (3D) renderings of the patient's anatomy, which are then used by a physician to assess the implant site and develop a surgical plan as described in commonly assigned U.S. Pat. No. 9,113,914 issued to Carroll, et al., which is incorporated by reference herein. The acquired image data not only includes data concerning the patient's anatomy, such as bones and/or cartilage, but the acquired image data also includes data concerning any foreign objects within the patient's body. The geometry and location of foreign objects within the patient's body is used when developing the surgical plan and preoperative analysis. In some embodiments, a foreign object is bone cement used to fuse the joint of the patient. However, one of ordinary skill in the art will understand that the foreign object can be an orthopedic implant and/or any other suitable surgical implant or device.

As another example, in some embodiments, the image data is used to determine one or more anatomical markers for alignment of one or more emitter marks 14. For example, an anatomical location, such as the upper portion of a tibia, the lower portion of a fibula, a hip joint, etc., may be imaged. Anatomical landmarks, such as portions of the imaged bones, may be selected as alignment locations at which one or more emitter marks 14 generated by an emitter-aligned surgical guide 2 are to be positioned. Multiple alignment positions may be selected based on a single imaged location, e.g., a superior end of a tibia, and/or based on multiple imaged locations, e.g., a superior end of a tibia and a hip joint. It will be appreciated that any suitable anatomical markers may be selected as alignment positions.

At step 306, one or more patient-specific surgical devices, such as an emitter-aligned surgical device 2, are fabricated and/or configured. In some embodiments, one or more emitter jigs 10a, 10b are positioned and/or formed in predetermined positions such that an emitter 12a, 12b coupled to each of the one or more emitter jigs 10a, 10b projects a predetermined emitter mark 14a, 14b at the previously selected alignment locations when the emitter-aligned surgical device 2 is properly aligned at a surgical site 102. In some embodiments, the emitter-aligned surgical device 2 is fabricated with a patient-specific surface. The emitter-aligned surgical device 2 will be sterilized and prepared for use during surgery as will be understood by one of ordinary skill in the art.

At step 308, access to the joint is established, such as by making an incision to expose the bony and/or cartilaginous surfaces of the joint. In some embodiments, the incision is made along the anterior of the patient's ankle joint to expose at least the tibia and talus.

At step 310, with the joint exposed, the first surface 8a, of the emitter-aligned surgical guide is placed in contact with a bony surface, a cartilaginous surface. The position of the first surface 8a relative to the surface of joint is adjusted by the surgeon until alignment marks 14a, 14b emitted by one or more emitters 12a, 12b coupled to the emitter-aligned surgical guide 2 are properly aligned with the predetermined anatomical positions. In some embodiments, further alignment may be provided by "locking" of emitter-aligned surgical guide 2 to a joint by aligning the complementary prominences and concavities of the patient-specific topography of the first surface 8a to the corresponding prominences and concavities of the tibia, talus, and/or other structure.

At step 312, with the position of emitter-aligned surgical guide 2 relative to one or more anatomical structures confirmed, k-wires or pins are inserted through the guide holes. For example, a pair of k-wires or pins are inserted into first bone by being guided by holes 70a, 70b to position the k-wires or pins at a specific location in the first bone.

At optional step 314, the emitter-aligned surgical guide 2 is removed from its engagement with first anatomical location 102. For example, the body 4 of the emitter-aligned surgical guide 2 may be slid over the k-wires or pins received within holes 70a, 70b such that a pair of k-wires or pins remains positioned within the one or more bones.

In some embodiments, the emitter-aligned surgical device 2 is not removed from its engagement with the first anatomical location 102. For example, emitter-aligned surgical device 2 can be configured to include a pre-attached, locator device, cutting guide, or drill guide such that the pre-attached device is positioned in the desired location relative to an anatomical structure of the patient when emitter-aligned surgical device 2 is positioned. Additionally or alternatively, other surgical tools or devices can be positioned relative to and/or coupled to the emitter-aligned surgical device while emitter-aligned surgical device 2 remains in its engagement with the first anatomical structure.

In various embodiments, a locator device, such as the locator device 60 illustrated in FIGS. 9-10, is coupled to the emitter-aligned surgical device 2 to guide insertion of one or more additional guide elements, such as a k-wire or pin. The inserted surgical alignment elements may be used to guide attachment or positioning of additional elements, such as cutting guides or drilling guides, prior to and/or after removing the emitter-aligned surgical guide 2 from the first anatomical location 102.

At step 316, surgical procedures may be performed using one or more guides formed integrally with, coupled to, and/or separate from the emitter-aligned surgical device 2. Examples of such procedures are shown and described in commonly assigned U.S. Pat. Nos. 8,808,297; 8,808,303; and 9,918,724, all of which are incorporated by reference herein in their entireties. These surgical procedures are only a few examples of possible surgical techniques that can be performed using the emitter-aligned surgical guides described herein.

The disclosed systems and methods described above advantageously utilize emitters to align surgical devices for use in one or more surgical procedures. These emitter-aligned surgical tools improve the accuracy of performing surgeries or other joint procedures.

In one embodiment, an emitter-aligned surgical guide includes a body extending between a first surface and a second surface. The body defining at least one hole extending from the first surface to the second surface. The emitter-aligned surgical guide further includes at least one alignment jig coupled to the second surface. The at least one alignment jig includes a jig arm extending from a first end coupled to the second surface of the body to a second end and an emitter support configured to couple an emitter device to the at least one alignment jig in a predetermined position relative to the body.

In some embodiments, the jig arm is configured to position the emitter support at a predetermined distance from the second surface of the body.

In some embodiments, the emitter support is configured to couple the emitter device at a predetermined angle relative to the jig arm.

In some embodiments, the at least one alignment jig comprises a first alignment jig and a second alignment jig.

In some embodiments, the first alignment jig is configured to position a first emitter device at a first predetermined location and a first predetermined angle with respect to the body and the second alignment jig is configured to position the second emitter device at a second predetermined location and a second predetermined angle with respect to the body.

In some embodiments, the first alignment jig is configured to position a first emitter device in a first plane relative to the body and the second alignment jig is configured to position a second emitter device in a second plane relative to the body.

In some embodiments, the first alignment jig is configured to position a first emitter device such that an emitted mark generated by the first emitter device references a first predetermined anatomical structure of a patient when the body is properly aligned with a target site, and wherein the second alignment jig is configured to position a second emitter device such that an emitted mark generated by the second emitter device references a second predetermined anatomical structure of a patient when the body is properly aligned with the target site In some embodiments, the first surface comprises a patient-specific topography.

In some embodiments, the emitter-aligned surgical guide includes a targeting guide coupled to the body.

In one embodiments, a system includes an emitter-aligned surgical guide, at least one fixation element, and at least one additional surgical guide. The emitter-aligned surgical guide includes a body extending between a first surface and a second surface and at least one alignment jig coupled to the second surface. The body defines at least one hole extending from the first surface to the second surface. The at least one alignment jig includes a jig arm extending from a first end coupled to the second surface of the body to a second end and an emitter support configured to couple an emitter device to the at least one alignment jig in a predetermined position relative to the body. The at least one fixation element is sized and configured to be received within the at least one hole defined by the body of the emitter-aligned surgical guide. The at least one additional surgical guide is configured to be coupled to one of the emitter-aligned surgical guide or the at least one fixation element.

In some embodiments, the jig arm is configured to position the emitter support at a predetermined distance from the second surface of the body.

In some embodiments, the emitter support is configured to couple the emitter device at a predetermined angle relative to the jig arm.

In some embodiments, the at least one alignment jig comprises a first alignment jig and a second alignment jig.

In some embodiments, the first alignment jig is configured to position a first emitter device at a first predetermined location and a first predetermined angle with respect to the body and the second alignment jig is configured to position the second emitter device at a second predetermined location and a second predetermined angle with respect to the body.

In some embodiments, the first alignment jig is configured to position a first emitter device in a first plane relative to the body and the second alignment jig is configured to position a second emitter device in a second plane relative to the body.

In some embodiments, the first alignment jig is configured to position a first emitter device such that an emitted mark generated by the first emitter device references a first predetermined anatomical structure of a patient when the body is properly aligned with a target site, and wherein the second alignment jig is configured to position a second emitter device such that an emitted mark generated by the second emitter device references a second predetermined anatomical structure of a patient when the body is properly aligned with the target site In some embodiments, the first surface of the emitter-aligned surgical guide comprises a patient-specific topography.

In some embodiments, the at least one additional surgical guide is selected from the group consisting essentially of: a targeting guide, a cutting guide, and a drill guide.

In one embodiment, a method includes a step of positioning an emitter-aligned surgical device adjacent to a first anatomical location. The emitter aligned surgical device includes a body extending between a first surface and a second surface and an alignment jig coupled to the second surface. The body defines at least one hole extending from the first surface to the second surface. The alignment jig includes a jig arm extending from a first end coupled to the second surface of the body to a second end and an emitter support coupled to an emitter device. The alignment jig positions the emitter device in a predetermined position relative to the body. The method further includes the steps of generating an emitted mark from the first emitter device and positioning the emitter-aligned surgical device at the first anatomical location such that the emitted mark from the first emitter device is aligned at a predetermined second anatomical location.

In some embodiments, the method further includes the step of inserting at least one fixation element through at least one hole defined in the body of the emitter-aligned surgical device when the emitted mark from the first emitter device is aligned at the predetermined second anatomical location.

Although the subject matter has been described in terms of exemplary embodiments, it is not limited thereto. Rather, the appended claims should be construed broadly, to include other variants and embodiments, which may be made by those skilled in the art.

What is claimed is:

1. An emitter-aligned surgical guide, comprising:
a body extending between a first surface and a second surface, the body defining at least one hole extending from the first surface to the second surface and configured to:
receive a fixation element, and
properly align with a target site;
a first alignment jig and a second alignment jig coupled to the second surface, comprising:

a jig arm extending from a first end coupled to the second surface of the body to a second end wherein the first alignment jig fixedly positions a first emitter device to project a first emitted mark in a first plane and is configured to position the first emitter device at a first predetermined location and a first predetermined angle with respect to the body and the second alignment jig fixedly positions a second emitter device to project a second emitted mark in a second, non-parallel plane, the first and second emitted marks being configured to reference distinct anatomical landmarks spaced apart from the guide body; and
an emitter support configured to fixedly couple at least one of the first and second emitter device to the at least one alignment jig in a predetermined position and angle relative to the body, wherein the first surface comprises a patient-specific topography configured to mate with a complementary anatomical surface of a patient thereby properly aligning the at least one hole with the target site, and further wherein the emitter support is positioned such that, when the patient-specific topography is securely seated on the patient's anatomy, the at least one of the first and second emitter device projects an emitted mark that references a predetermined second anatomical location spaced apart from the first surface.

2. The device of claim 1, wherein the jig arm is configured to position the emitter support at a predetermined distance from the second surface of the body.

3. The device of claim 1, wherein the emitter support is configured to couple the at least one of the first and second emitter device at a predetermined angle relative to the jig arm.

4. The device of claim 1, wherein the first alignment jig is configured to position the first emitter device in a first plane relative to the body and the second alignment jig is configured to position the second emitter device in a second plane relative to the body.

5. The device of claim 1, wherein the first alignment jig is configured to position the first emitter device such that the emitted mark generated by the first emitter device is configured to reference a first predetermined anatomical structure of a patient when the body is properly aligned with the target site, and wherein the second alignment jig is configured to position the second emitter device such that the emitted mark generated by the second emitter device is configured to reference one of the distinct anatomical landmarks of a patient when the body is properly aligned with the target site.

6. The device of claim 1, comprising a targeting guide coupled to the body.

7. A system, comprising:
an emitter-aligned surgical guide, comprising:
a body extending between a first surface and a second surface, the body defining at least one hole extending from the first surface to the second surface and configured to properly align with a target site;
a first alignment jig and a second alignment jig coupled to the second surface, the first alignment jig comprising:
a jig arm extending from a first end coupled to the second surface of the body to a second end wherein the first alignment jig is configured to position a first emitter device at a first predetermined location and a first predetermined angle with respect to the body and a second alignment jig is configured to position a second emitter device at a second predetermined location and a second predetermined angle with respect to the body; and an emitter support configured to fixedly couple at least one of the first and second emitter device to the at least one alignment jig in a predetermined position and angle relative to the body, wherein the first surface comprises a patient-specific topography configured to mate with a complementary anatomical surface of a patient thereby properly aligning the at least one hole with the target site, and further wherein the emitter support is positioned such that, when the patient-specific topography is properly seated on the patient's anatomy, the at least one of the first and second emitter device projects an emitted mark that references a predetermined second anatomical location spaced apart from the first surface; and at least one guide element sized and configured to be received within the at least one hole defined by the body of the emitter-aligned surgical guide; and at least one additional surgical guide configured to be coupled to one of the emitter-aligned surgical guide or the at least one guide element.

8. The system of claim 7, wherein the jig arm is configured to position the emitter support at a predetermined distance from the second surface of the body.

9. The system of claim 7, wherein the emitter support is configured to couple the at least one of the first and second emitter device at a predetermined angle relative to the jig arm.

10. The system of claim 7, wherein the first alignment jig is configured to position a first emitter device in a first plane relative to the body and the second alignment jig is configured to position a second emitter device in a second plane relative to the body.

11. The system of claim 7, wherein the first alignment jig is configured to position a first emitter device such that an emitted mark generated by the first emitter device is configured to reference a first predetermined anatomical structure of a patient when the body is properly aligned with the target site, and wherein the second alignment jig is configured to position a second emitter device such that an emitted mark generated by the second emitter device is configured to reference a second predetermined anatomical structure of a patient when the body is properly aligned with the target site.

12. The system of claim 7, wherein the first surface of the emitter-aligned surgical guide comprises a patient-specific topography.

13. The system of claim 7, wherein the at least one additional surgical guide is selected from the group consisting essentially of: a targeting guide, a cutting guide, and a drill guide.

14. A method, comprising:

positioning an emitter-aligned surgical device adjacent to a first anatomical location, wherein the emitter aligned surgical device comprises:

a body extending between a first surface and a second surface, the body defining at least one hole extending from the first surface to the second surface;

an alignment jig coupled to the second surface, the alignment jig comprising:

a jig arm extending from a first end coupled to the second surface of the body to a second end including a first alignment jig and a second alignment jig wherein the first alignment jig is configured to position a first emitter device at a first predetermined location and a first predetermined angle with respect to the body and a second alignment jig is configured to position a second emitter device at a second predetermined location and a second predetermined angle with respect to the body; and an emitter support fixedly coupled to at least one of the first and second emitter device, wherein the alignment jig positions the at least one of the first and second emitter device in a predetermined position and angle relative to the body, wherein the first surface comprises a patient-specific topography configured to mate with a complementary anatomical surface of a patient thereby properly aligning the at least one hole with the target site, and further wherein the emitter support is positioned such that, when the patient-specific topography is properly seated on the patient's anatomy, the at least one of the first and second emitter device projects an emitted mark that references a predetermined second anatomical location spaced apart from the first surface;

generating an emitted mark from the at least one of the first and second emitter device; and positioning the emitter-aligned surgical device at the first anatomical location such that the emitted mark from the at least one of the first and second emitter device is aligned at a predetermined second anatomical location.

15. The method of claim 14, comprising inserting at least one guide element through at least one hole defined in the body of the emitter-aligned surgical device when the emitted mark from the at least one of the first and second emitter device is aligned at the predetermined second anatomical location.

* * * * *